US00PP14240P29

(12) United States Plant Patent
Bradford

(10) Patent No.: US PP14,240 P2
(45) Date of Patent: Oct. 14, 2003

(54) NECTARINE TREE NAMED 'GIANT PEARL'

(50) Latin Name: *Prunus persica*
Varietal Denomination: 'Giant Pearl'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/299,084

(22) Filed: Nov. 19, 2002

(51) Int. Cl.[7] ..... A01H 5/00
(52) U.S. Cl. ..... Plt./188
(58) Field of Search ..... Plt./188

(56) References Cited

U.S. PATENT DOCUMENTS

PP6,363 P 11/1988 Bradford
PP7,049 P 10/1989 Bradford
PP8,461 P 11/1993 Bradford
PP9,358 P 11/1995 Bradford

*Primary Examiner*—Bruce R. Campell
*Assistant Examiner*—W C Haas

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described approximately the second week in August, with first picking on Aug. 9, 2002. The fruit is uniformly large in size, excellent in flavor, globose in shape, clingstone in type, very firm in texture, white in flesh color, and mostly red in skin color. The variety was developed as a first generation cross using 'Summer Bright' (U.S. Plant Pat. No. 7,049) yellow flesh nectarine as the selected seed parent and an unnamed white flesh nectarine seedling as the selected pollen parent.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'GIANT PEARL'. The present variety was hybridized by me in 1994, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Summer Bright' (U.S. Plant Pat. No. 7,049) yellow flesh nectarine as the selected seed parent and an unnamed white flesh nectarine seedling as the selected pollen parent. This unnamed pollen parent was previously developed as a first generation cross between 'Bradcrim' (U.S. Plant Pat. No. 8,461) white flesh nectarine and 'August Red' (U.S. Plant Pat. No. 6,363) yellow flesh nectarine. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Summer Bright' (U.S. Plant Pat. No. 7,049) nectarine, by producing nectarines that are globose in shape, firm in texture, clingstone in type, and almost full red in skin color, but is very distinguished therefrom and an improvement thereon by producing fruit that is white instead of yellow in flesh color, that is subacid instead of acid in flavor, and that matures about seventeen days later.

The present variety is similar to one of its selected pollen grandparent, 'Bradcrim' (U.S. Plant Pat. No. 8,461) nectarine, by producing nectarines that are white in flesh color, almost full red in skin color, and subacid in flavor, but is quite distinguished therefrom and an improvement thereon by producing fruit that is much larger in size, that is firmer in texture, that is clingstone instead of freestone in type, and that matures about one month later.

The present variety is similar to its other selected pollen grandparent, 'August Red' (U.S. Plant Pat. No. 6,363) nectarine, by producing nectarines that are clingstone in type, almost full red in skin color, and firm in texture, but is quite distinguished therefrom and an improvement thereon by producing fruit that is white instead of yellow in flesh color, subacid instead of acid in flavor, and that matures about twenty days earlier.

The present variety is most similar to 'Fire Pearl' (U.S. Plant Pat. No. 9,358) nectarine by producing white flesh clingstone nectarines that are firm in texture, mostly red in skin color, and sweet subacid in flavor, but is distinguished therefrom and an improvement thereon by having reniform instead of globose leaf glands, by having a small non-showy instead of large showy blossom, and by producing nectarines that are much larger in size and mature about ten days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 15, 2002, on the original tree during its eighth growing season. All major color code designations are by reference to the Inter-Society Color Council, National Bureau of Standards. Common color names are also used occasionally.

TREE

Size: Medium, reaching a height of 9' [2.74 m.] and a spread of 8' [2.44 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and open.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

*Size.*—Medium, with a maximum diameter of 2¾" [70 mm.] after the eighth growing season.

*Texture.*—Shaggy.

*Bark color.*—Dark grayish reddish brown [47. d.gy.rBr].

*Lenticles.*—Approximate Number Per Square Inch: 14. Color: Light orange yellow [70. l.OY]. Average Size: ¼" [6.4 mm.].

Branches:

*Size.*—Diameter of limb is 1" [25 mm.] measured 12" above the secondary fork, typical of *Prunus persica*, and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Moderate brown [58. m.Br].

*Lenticels.*—Approximate Number Per Square Inch: 40. Color: Light orange yellow [70. l.OY]. Typical size: 1/16" to 3/16" [1.6–4.8 mm.].

Leaves:

*Size.*—Medium. Average Length: 5⅞" [149 mm.]. Average width: 1⅝" [41 mm.].

*Arrangement.*—Alternate.

*Thickness.*—Medium.

*Form.*—Elliptical.

*Apex.*—Acuminate.

*Base.*—Acute, with an average base angle of 90 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Number: 2 per leaf, up to 6 per growing tip. Average Length: ¼" [6.4 mm.]. Color: Brilliant yellow green [116. brill.YG] with Deep red [13. deep R] margins.

*Glands.*—Number: 2 to 4. Position: Mostly alternate, positioned on both the petiole and base of blade. Size: Medium. Form: Reniform. Color: Brilliant yellow green [116. brill.YG] with Moderate reddish brown [43. m.rBr] centers on older glands.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically 7/16" [11.1 mm.] 1 week before bloom.

*Form.*—Not appressed.

*Surface.*—Pubescent.

*Color.*—Moderate purplish red [258. m.pR].

Flowers: Perfect, complete, perigynous, usually a single pistil, typically thirty or more stamens, five sepals and petal locations alternately positioned.

*Type.*—Non-showy, small.

*Average flower diameter.*—1 5/16" [33.3 mm.].

*Number of petals.*—Almost always five.

*Petal shape.*—Oval.

*Petal margin.*—Somewhat wavy.

*Average petal diameter.*—⅜" [9.5 mm.].

*Average petal length.*—½" [12.7 mm.].

*Petal apex.*—Rounded.

*Petal base.*—Acute.

*Petal color.*—Light pink [4. l.Pk] toward the center becoming Moderate purplish red [258. m.pR] toward the margin.

*Anther color.*—Dark reddish orange [38. d.rO] over a Brilliant orange yellow [67. brill.OY] center.

*Stigma color.*—Light greenish yellow [101. l.gY].

*Sepal color.*—Grayish purplish red [262. gy.pR].

*Sepal length.*—3/16" [5 mm.].

*Sepal width.*—5/32" [4 mm.].

*Average pistil length.*—9/16" [14.3 mm.].

*Average stamen length.*—7/16"[11.1 mm.].

*Fragrance.*—Moderate when nectar is present.

*Blooming period.*—Medium compared with other varieties.

*Onset of bloom.*—One percent on Mar. 4, 2002.

*Date of full bloom.*—Mar. 11, 2002.

*Duration of bloom.*—One to two weeks, dependent on ambient temperature.

*Number per cluster.*—1 to 3 with single flowers most common.

FRUIT

Maturity when described: Firm ripe, Aug. 15, 2002.

Date of first picking: Aug. 9, 2002.

Date of last picking: Aug. 20, 2002.

Size: Uniform, very large.

*Average diameter axially.*—3⅛" [79.4 mm.].

*Average diameter across suture plane.*—3⅛" [79.4 mm.].

*Typical weight.*—10 ounces [283 grams].

Form: Globose, mostly symmetrical.
*Longitudinal section form.*—Circular.
*Transverse section through diameter.*—Circular.
Suture: A sharp groove toward the base, becoming shallow and rounded along the sides, deepening toward the apex, and discontinuing with a slight depression just beyond the pistil point.
Ventral surface: Rounded, lipped stronger toward the apex.
Lips: Unequal, as one lip usually forms a minor suture bulge along the side.
Cavity: Flaring, circular, suture showing on one side, Yellowish white white [92. ywhite] stem markings typical.
*Depth.*—5/8" [15.9 mm.].
*Breadth.*—1 1/8" [28.6 mm.].
Base: Rounded to slightly truncate.
Apex: Rounded and slightly cuneate when viewed along the suture.
Pistil point: Both apical and oblique, short, usually depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Slight.
*Color.*—Dark red [16. d.R] smoothly blending to Moderate red [15. m.R], an occasional Pale yellow green [121. p.YG] sun protected area, and Light orange yellow [73. l.OY] freckling on the sides and toward the apex.
Flesh:
*Color.*—Yellowish white [92. yWhite] with Dark red [16. d.R] streaking near the stone.
*Surface of pit cavity.*—Dark red [16. d.R] fibers breaking when twisted from the stone.
*Amygdalin.*—Scarce.
*Juice.*—Abundant, rich.
*Texture.*—Very firm, crisp.
*Fibers.*—Abundant, fine.
*Ripens.*—Slightly earlier toward the apex.
*Flavor.*—Subacid and sweet, averaging 16 to 18 brix.
*Aroma.*—Slight.
*Eating quality.*—Very good.

STONE

Type: Clingstone.
Form: Oval.
Hilum: Narrow, oblong.
Base: Straight.
Apex: Acute to acuminate, typically with a very sharp 3/16" [4.8 mm.] tip.
Sides: Equal.
Surface: Horizontally furrowed near the apex becoming vertical toward the base with minor pitting from the base to center.
Ridges: Jagged toward the base.
External color of stone: Deep reddish brown [41. deep rBr].
Pit wall color when cracked: Moderate brown [58. m.Br].
Surface color of stone cavity: Strong brown [55. s.Br].
Average pit wall thickness: 1/4" [6.4 mm.].
Average width: 1 1/8" [28.6 mm.].
Average length: 1 7/16" [36.5 mm.].
Average breadth: 13/16" [20.6 mm.].
Tendency to split: None observed.
Kernel:
*Form.*—Oval.
*Skin color.*—Pale yellow [89. p.Y] when freshly removed.
*Pellicle color.*—Light grayish yellowish brown [79. l.gy.yBr].
*Vein color.*—Deep yellowish brown [75. deep yBr].
*Taste.*—Bitter.
*Viable.*—Yes.
*Average width.*—9/16" [14.3 mm.].
*Average length.*—7/8" [22.2 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shippinq quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Fire Pearl' (U.S. Plant Pat. No. 9,358) nectarine by producing white flesh clingstone nectarines that are firm in texture, mostly red in skin color, and sweet subacid in flavor, but is distinguished therefrom and an improvement thereon by having reniform instead of globose leaf glands, by having small non-showy instead of large showy blossoms, and by producing nectarines that are much larger in size and mature about ten days later.

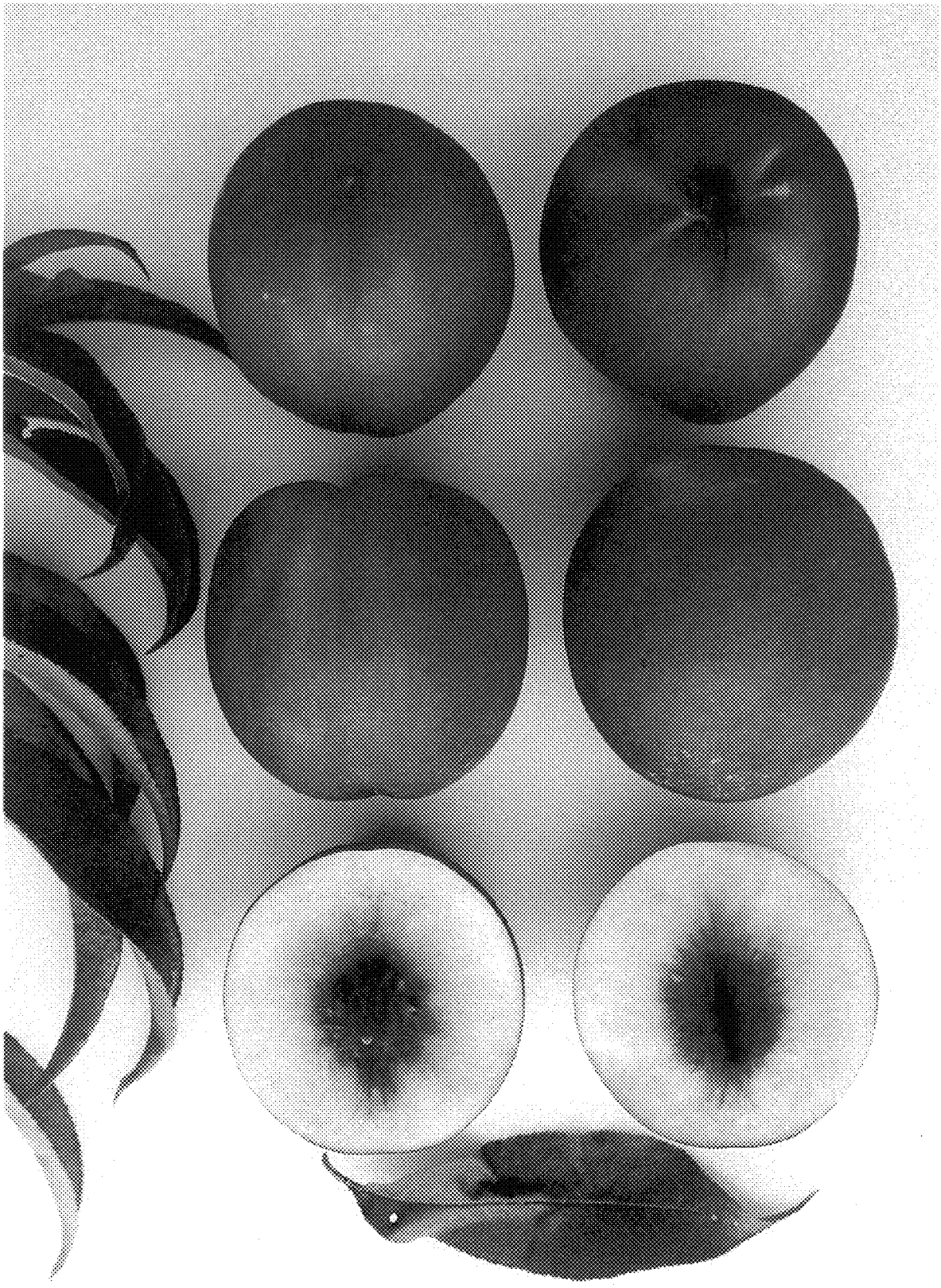

* * * * *